(12) United States Patent
Zhang et al.

(10) Patent No.: US 7,328,063 B2
(45) Date of Patent: Feb. 5, 2008

(54) METHOD AND APPARATUS FOR ARRHYTHMIA CLASSIFICATION USING ATRIAL SIGNAL MAPPING

(75) Inventors: Yunlong Zhang, Mounds View, MN (US); Julie Thompson, Circle Pines, MN (US); James O. Gilkerson, Stillwater, MN (US); Yongxing Zhang, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 298 days.

(21) Appl. No.: 11/000,133

(22) Filed: Nov. 30, 2004

(65) Prior Publication Data

US 2006/0116594 A1 Jun. 1, 2006

(51) Int. Cl.
*A61B 5/04* (2006.01)
(52) U.S. Cl. .................................. 600/515; 600/518
(58) Field of Classification Search ................. 600/515
See application file for complete search history.

(56) References Cited

U.S. PATENT DOCUMENTS

| | | | |
|---|---|---|---|
| 5,243,980 A | 9/1993 | Mehra | |
| 5,482,037 A | 1/1996 | Borghi | |
| 5,697,377 A | 12/1997 | Wittkampf | |
| 5,755,761 A | 5/1998 | Obino | |
| 5,873,897 A * | 2/1999 | Armstrong et al. | 607/14 |
| 5,891,170 A * | 4/1999 | Nitzsche et al. | 607/4 |
| 5,978,707 A | 11/1999 | Krig et al. | |
| 6,151,524 A | 11/2000 | Krig et al. | |
| 6,223,078 B1 | 4/2001 | Marcovecchio | |
| 6,230,055 B1 | 5/2001 | Sun et al. | |
| 6,266,554 B1 | 7/2001 | Hsu et al. | |
| 6,275,732 B1 | 8/2001 | Hsu et al. | |
| 6,308,095 B1 | 10/2001 | Hsu et al. | |
| 6,317,632 B1 | 11/2001 | Krig et al. | |
| 6,449,503 B1 | 9/2002 | Hsu | |
| 6,456,871 B1 | 9/2002 | Hsu et al. | |
| 6,484,055 B1 | 11/2002 | Marcovecchio | |
| 6,493,579 B1 | 12/2002 | Gilkerson et al. | |
| 6,496,731 B1 | 12/2002 | Lovett | |
| 6,522,914 B1 | 2/2003 | Huvelle et al. | |
| 6,522,917 B1 | 2/2003 | Hsu et al. | |

(Continued)

OTHER PUBLICATIONS

Hsu, William, "System and Method for Classifying Tachycardia Arrythmias Having 1:1 Atrial to Ventricualr Rhythms", U.S. Appl. No. 09/417,588, filed Oct. 13, 1999, 39 pgs.

(Continued)

*Primary Examiner*—Carl Layno
*Assistant Examiner*—Brian T. Gedeon
(74) *Attorney, Agent, or Firm*—Schwegman, Lundberg & Woessner, P.A.

(57) ABSTRACT

An implantable medical device senses a plurality of electrograms from substantially different atrial locations, detects regional depolarizations from the electrograms, and analyzes timing relationships among the regional depolarizations. The timing relationships provide a basis for effective therapy control and/or prognosis of certain cardiac disorders. In one embodiment, an atrial activation sequence is mapped to show the order of occurrences of the regional depolarizations during an atrial depolarization for classifying a detected tachyarrhythmia by its origin. In another embodiment, conduction time between two atrial locations is measured for monitoring the development of an abnormal atrial conditions and/or the effect of a therapy.

47 Claims, 9 Drawing Sheets

U.S. PATENT DOCUMENTS

| | | |
|---|---|---|
| 6,522,925 B1 | 2/2003 | Gilkerson et al. |
| 6,539,256 B1 | 3/2003 | KenKnight et al. |
| 6,584,362 B1 | 6/2003 | Scheiner et al. |
| 6,662,045 B2 * | 12/2003 | Zheng et al. .................. 607/5 |
| 6,671,548 B1 | 12/2003 | Mouchawar et al. |
| 6,687,540 B2 | 2/2004 | Marcovecchio |
| 6,708,058 B2 | 3/2004 | Kim et al. |
| 6,728,572 B2 | 4/2004 | Hsu et al. |
| 6,736,808 B1 | 5/2004 | Motamedi et al. |
| 6,748,269 B2 | 6/2004 | Thompson et al. |
| 6,909,916 B2 | 6/2005 | Spinelli et al. |
| 6,978,177 B1 | 12/2005 | Chen et al. |
| 6,980,860 B2 * | 12/2005 | Stadler et al. ................ 607/14 |
| 7,031,764 B2 | 4/2006 | Schwartz et al. |
| 7,058,443 B2 * | 6/2006 | Struble ....................... 600/520 |
| 7,174,209 B2 * | 2/2007 | Thompson et al. ............ 607/9 |
| 2002/0091333 A1 | 7/2002 | Hsu et al. |
| 2002/0107552 A1 | 8/2002 | Krig et al. |
| 2002/0123768 A1 | 9/2002 | Gilkerson |
| 2003/0105491 A1 | 6/2003 | Gilkerson et al. |
| 2003/0109914 A1 | 6/2003 | Westlund et al. |
| 2003/0114889 A1 | 6/2003 | Huvelle |
| 2004/0093035 A1 | 5/2004 | Schwartz et al. |
| 2004/0116820 A1 | 6/2004 | Daum et al. |
| 2004/0116972 A1 | 6/2004 | Marcovecchio |
| 2004/0158165 A1 | 8/2004 | Yonce et al. |
| 2005/0010257 A1 | 1/2005 | Lincoln et al. |
| 2005/0149134 A1 | 7/2005 | McCabe et al. |
| 2005/0197674 A1 | 9/2005 | McCabe et al. |
| 2005/0256544 A1 | 11/2005 | Thompson |
| 2006/0015148 A1 | 1/2006 | McCabe et al. |
| 2006/0074330 A1 | 4/2006 | Smith et al. |
| 2006/0095083 A1 | 5/2006 | Zhang et al. |
| 2006/0111643 A1 | 5/2006 | Cazares et al. |
| 2006/0161069 A1 | 7/2006 | Li |
| 2006/0178704 A1 * | 8/2006 | Elahi et al. .................... 607/5 |

OTHER PUBLICATIONS

Kim, Jaeho, et al., "Rhythm Discrimination of Sudden Onset and One-to-One Tachyarrhythmia", U.S. Appl. No. 11/276,213, filed Feb. 17, 2006, 33 Pages.

Li, Dan, "Method and Apparatus for Cardiac Arrhythmia Classification Using Sample Entropy", U.S. Appl. No. 11/151,567, filed Jun. 13, 2005, 43 Pgs.

Li, Dan, "Method and Apparatus for Morphology-Based Arrhythmia Classification Using Cardiac and Other Physiological Signals", U.S. Appl. No. 11/316,332, filed Dec. 22, 2005, 63 Pages.

Li, Dan, "Method and Apparatus for Rate-Dependent Morphology-Based Cardiac Arrhythmia Classification", U.S. Appl. No. 11/151,567, filed Jun. 13, 2005, 53 pgs.

Li, Dan , et al., "Method and Apparatus for Selecting and Timing Anti-Tachyarrhythmia Pacing Using Cardiac Signal Morphology", U.S. Appl. No. 11/276,162, filed Feb. 16, 2006, 42 pgs.

Sweeney, Robert J., "Tachyarrhythmia Detection and Discrimination Based on Curvature Parameters", U.S. Appl. No. 10/607,818, filed Jun. 27, 2003, 59 pgs.

* cited by examiner

METHOD AND APPARATUS FOR ARRHYTHMIA CLASSIFICATION USING ATRIAL SIGNAL MAPPING

TECHNICAL FIELD

This document relates generally to cardiac rhythm management (CRM) systems and particularly, but not by way of limitation, to such a system providing for detection and classification of tachyarrhythmias.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract at a normal sinus rate.

Tachyarrhythmia occurs when the heart contracts at a rate higher than the normal sinus rate. Tachyarrhythmia generally includes ventricular tachyarrhythmia (VT) and supraventricular tachyarrhythmia (SVT). VT occurs, for example, when a pathological conduction loop formed in the ventricles through which electrical impulses travel circularly within the ventricles, or when a pathologically formed electrical focus generates electrical impulses from the ventricles. SVT can be physiologic (e.g., sinus tachycardia) or pathologic (e.g., atrial fibrillation). The physiologic sinus tachycardia occurs when the SA node generates the electrical impulses at a particularly high rate. A pathologic SVT occurs, for example, when a pathologic conduction loop forms in an atrium or both atria. Fibrillation occurs when the heart contracts at a tachyarrhythmia rate with an irregular rhythm. Ventricular fibrillation (VF), as a ventricular arrhythmia with an irregular conduction, is a life threatening condition requiring immediate medical treatment such as ventricular defibrillation. Atrial fibrillation (AF), as an SVT with an irregular rhythm, though not directly life threatening, also needs medical treatment such as atrial defibrillation to restore a normal cardiac function and prevents the deterioration of the heart.

An understanding of the nature of a detected tachyarrhythmia, including its origin, ensures effective and efficient treatment. For example, anti-tachycardia pacing, cardioversion, and defibrillation are among therapies treating tachyarrhythmias by delivering electrical energy to the heart. To be effective, the type of tachyarrhythmia, including its origin, is to be determined for selecting the right type therapy and the right region to which the electrical energy is delivered. When the atrial rate of depolarizations (or contractions) is substantially different from the ventricular rate of depolarizations (or contractions) during a detected tachyarrhythmia, the atrial and ventricular rates of depolarizations (or contractions) provide for a basis for locating where the tachyarrhythmia originates. However, there is a need to locate where the tachyarrhythmia originates when the atrial depolarizations and the ventricular depolarizations present a one-to-one (1:1) relationship.

SUMMARY

An implantable medical device senses a plurality of electrograms from substantially different atrial locations, detects regional depolarizations from the electrograms, and analyzes timing relationships among the regional depolarizations. The timing relationships provide a basis for effective therapy control and/or prognosis of certain cardiac disorders.

In one embodiment, a CRM system includes a high RA (HRA) electrode, an LA electrode, an atrial septal electrode, a ventricular electrode, and an implantable medical device. The HRA electrode is to be placed near the SA node to sense an RA electrogram. The LA electrode is to be placed near the LA to sense an LA electrogram. The atrial septal electrode is to be placed in or near the atrial septum to sense an atrial septal electrogram. The ventricular electrode is to be placed in or near a ventricle to sense a ventricular electrogram. The implantable medical device includes an arrhythmia detection circuit to detect tachyarrhythmias and an arrhythmia classification circuit to classify the detected tachyarrhythmias. The arrhythmia classification circuit includes an atrial signal mapping module and an atrial pattern analyzer. The atrial signal mapping module maps an atrial activation sequence based on the RA electrogram, the LA electrogram, and atrial septal electrogram. The atrial activation sequence indicates an order of regional depolarizations during an atrial depolarization. The atrial pattern analyzer classifies each detected tachyarrhythmia based on the atrial activation sequence.

In one embodiment, a tachyarrhythmia detection and classification system includes a sensing circuit, a rate detection circuit, an arrhythmia detection circuit, and an arrhythmia classification circuit. The sensing circuit senses a plurality of atrial electrograms and at least one ventricular electrogram. The rate detection circuit detects an atrial rate from at least one of the atrial electrograms and a ventricular rate from the ventricular electrogram. The arrhythmia detection circuit detects a tachyarrhythmia based on at least one of the atrial rate and the ventricular rate. The arrhythmia classification circuit includes a 1:1 tachyarrhythmia detector, an atrial signal mapping module, and an atrial pattern analyzer. The 1:1 tachyarrhythmia detector classifies the detected tachyarrhythmia as a 1:1 tachyarrhythmia when the atrial rate and the ventricular rate are substantially equal. The atrial signal mapping module maps an atrial activation sequence based on the atrial electrograms. The atrial activation sequence indicates an order of regional depolarizations during an atrial depolarization. The atrial pattern analyzer classifies the 1:1 tachyarrhythmia based on the atrial activation sequence.

In one embodiment, a CRM system provides for monitoring of prognostic factors for atrial fibrillation and heart failure. The CRM system includes two electrodes, a sensing circuit, an event detection circuit, and an inter-atrial interval measurement circuit. One electrode is to be placed in the RA or superior vena cava near the SA node. The other electrode is to be placed in the coronary sinus or coronary vein near the LA. The sensing circuit senses an RA electrogram and an LA electrogram through the electrodes. The event detection circuit detects an RA event from the RA electrogram and an LA event from the LA electrogram during an atrial depolarization. The inter-atrial interval measurement circuit measures an inter-atrial interval between the RA event and the LA event.

In one embodiment, a coronary lead provides for sensing of one or more of an LA electrogram, an atrial septal electrogram, and an RA electrogram. The coronary lead includes an elongate lead body with a primary end and a distal end. The primary end is coupled to a connector for connecting to an implantable medical device. At least an LA electrode, an atrial septal electrode, and an HRA electrode are incorporated into the coronary lead. The LA electrode is to be placed in the coronary sinus or coronary vein near the LA. The atrial septal electrode is to be placed in the coronary sinus near the atrial septum. The HRA electrode is to be placed in the RA or the superior vena cava near the SA node. The LA electrode, the atrial septal electrode, and the HRA electrode are each connected to one of a plurality of conductors that are disposed within the lead body and connected to the connector.

In one embodiment, an RA lead provides for sensing of one or more RA electrograms. The RA lead includes an elongate lead body with a primary end and a distal end. The primary end is coupled to a connector for connecting to an implantable medical device. At least an HRA electrode and a second RA electrode are incorporated into the RA lead. The HRA electrode is to be placed in the RA or the superior vena cava near the SA node. The second RA electrode is to be placed in the RA in or near the atrial septum. The HRA electrode and the second RA electrode are each connected to one of a plurality of conductors that are disposed within the lead body and connected to the connector.

In one embodiment, a method provides for classification of a tachyarrhythmia by its origin. An atrial activation sequence is received. The atrial activation sequence indicates an order of occurrence of an RA event, an atrial septal event, and an LA event during an atrial depolarization. The tachyarrhythmia is classified as a tachyarrhythmia of RA origin if the RA event occurs first in the atrial activation sequence, as a tachyarrhythmia of LA origin if the LA event occurs first in the atrial activation sequence, and as a tachyarrhythmia of atrial septal or ventricular origin if the atrial septal event occurs first in the atrial activation sequence.

In one embodiment, a method provides for detection and classification of tachyarrhythmias. A plurality of atrial electrograms and at least one ventricular electrogram are sensed. The atrial electrograms indicates regional depolarizations in substantially different atrial locations. An atrial rate is detected from at least one of the atrial electrograms. A ventricular rate is detected from the ventricular electrogram. A tachyarrhythmia is detected based on at least one of the atrial rate and the ventricular rate. The detected tachyarrhythmia is classified as a 1:1 tachyarrhythmia when the atrial rate and the ventricular rate are substantially equal. Following the classification of the detected tachyarrhythmia as the 1:1 tachyarrhythmia, an atrial activation sequence is mapped based on the atrial electrograms. The atrial activation sequence indicates an order of occurrence of the regional depolarizations in the substantially different atrial locations. The 1:1 tachyarrhythmia is classified based on the atrial activation sequence.

In one embodiment, a method provides for monitoring of a heart. An RA electrogram is sensed using an electrode placed in the RA or the superior vena cava near the SA node. An LA electrogram is sensed using an electrode placed in the coronary sinus or coronary vein near the LA. An RA event is detected from the RA electrogram, and an LA event is detected from the LA electrogram, for each atrial depolarization. An inter-atrial interval is measured as the time interval between the RA event and the LA event.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
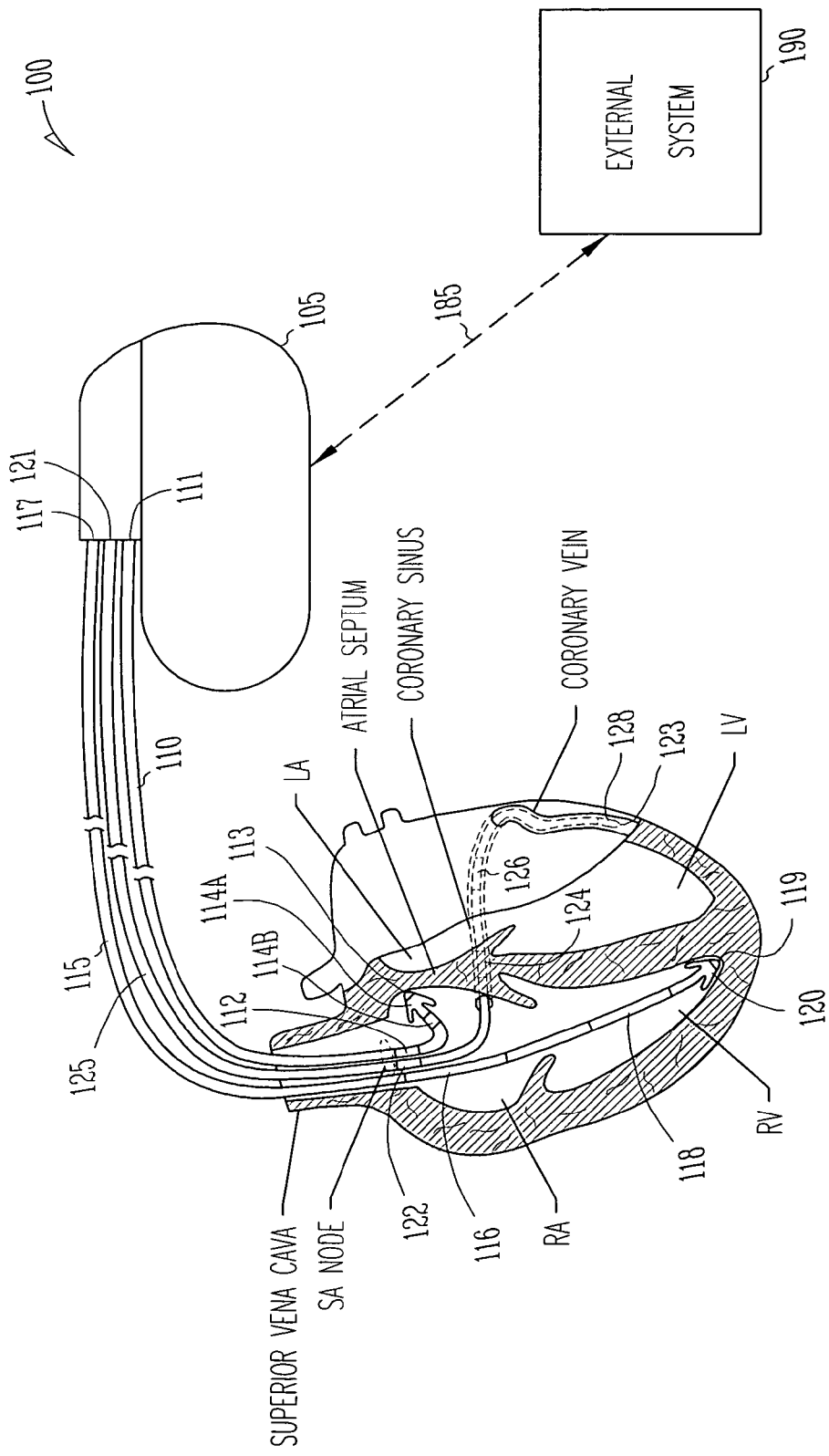
FIG. 1 is an illustration a CRM system including an arrhythmia detection and classification circuit and/or an inter-atrial interval monitoring circuit and portions of an environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a CRM system that detects and classifies tachyarrhythmias and/or monitors inter-atrial conduction intervals. The origin of each tachyarrhythmia classified as a 1:1 tachyarrhythmia is located by atrial signal mapping. The 1:1 tachyarrhythmia, characterized by a one-to-one association between atrial and ventricular depolarizations, is indicated by substantially equal atrial and ventricular rates. Electrograms are sensed from multiple atrial sites and at least one ventricular site. The atrial signal mapping results in an atrial activation sequence showing the order of regional depolarization at the multiple atrial sites during an atrial depolarization, thus allowing for localization of the origin of the 1:1 tachyarrhythmia. For example, an RA electrogram, an atrial septal electrogram, an LA electrogram, and a ventricular (RV or LV) electrogram are sensed. A 1:1 tachyarrhythmia is classified as a tachyarrhythmia of RA origin (or SVT of RA origin) if RA depolarizes first during the atrial depolarization, a tachyarrhythmia of LA origin (or SVT of LA origin) if LA depolarizes first during the atrial depolarization, and a tachyarrhythmia of atrial septal origin or ventricular origin with one-to-one retrograde conduction via the atrioventricular (AV) node if the atrial septum depolarizes first during the atrial depolarization. Morphological analysis is applied to further discriminate between a tachyarrhythmia of atrial septal origin (or SVT of atrial septal origin) and a tachyarrhythmia of ventricular origin with one-to-one retrograde conduction via the AV node (or VT). The classification of the 1:1 tachyarrhythmia is used for diagnostic and/or therapy control purposes. Electrograms sensed from different atrial sites also provide for measurement of an inter-atrial interval, which is a time interval between two regional depolarizations at substantially different atrial location during an atrial depolarization. Abnormalities in the inter-atrial interval serve as factors prognosticating conditions such as heart failure and AF.

FIG. 1 is an illustration a CRM system 100 and portions of an environment in which system 100 operates. CRM system 100 includes an implantable medical device 105 that is electrically coupled to a heart through leads 110, 115, and 125. An external system 190 communicates with implantable medical device 105 via a telemetry link 185.

Implantable medical device 105 includes a hermetically sealed can housing an electronic circuit that senses physiological signals and delivers therapeutic electrical pulses. The hermetically sealed can also functions as an electrode for sensing and/or pulse delivery purposes. In one embodiment, implantable medical device 105 includes an arrhythmia detection and classification circuit that detects and classifies tachyarrhythmias. If a detected tachycardia is classified as a 1:1 tachyarrhythmia, it is further classified by determining its origin based on at least an atrial signal mapping. Exemplary embodiments of the arrhythmia detection and classification circuit and method are described in detail below with reference to FIGS. 2-9. In one embodiment, implantable medical device 105 includes an inter-atrial interval monitoring circuit to measure an inter-atrial interval for cardiac condition prognosis or therapy monitoring purposes. Exemplary embodiments of the inter-atrial interval monitoring circuit and method are described in detail below with reference to FIGS. 10-12.

Lead 110 is a pacing lead. In one embodiment, as illustrated in FIG. 1, lead 110 is an RA pacing lead that includes an elongate lead body having a proximal end 111 and a distal end 113. Proximal end 111 is coupled to a connector for connecting to implantable medical device 105. Distal end 113 is configured for placement in the RA in or near the atrial septum. Lead 110 includes a high RA (HRA) electrode 112, an atrial septal tip electrode 114A, and an atrial septal ring electrode 114B. HRA electrode 112 is a pacing-sensing electrode incorporated into the lead body in a location suitable for placement in the RA or the superior vena cava near the SA node. Atrial septal electrodes 114A and 114B are pacing-sensing electrodes incorporated into the lead body at or near distal end 113 for placement in or near the atrial septum. Electrodes 112, 114A, and 114B are each electrically coupled to implantable medical device 105 through a conductor disposed within the lead body. HRA electrode 112 allows for sensing an RA electrogram indicative of depolarizations in an upper RA region including the SA node and its vicinity and delivering pacing pulses to that region. In one embodiment, HRA electrode 112 is a ring electrode incorporated onto the elongate lead body. The distance between distal end 113 and HRA electrode 112 is determined such that when distal end 113 is placed in the atrial septum, electrode 112 is in a location suitable for sensing the RA electrogram indicative of depolarizations in the upper RA region including the SA node and its vicinity and delivering pacing pulses to that region. Atrial septal electrodes 114A and/or 114B allow for sensing an atrial septal electrogram indicative of depolarizations in the atrial septal region and delivering pacing pulses to that region.

Lead 115 is a defibrillation lead. In one embodiment, as illustrated in FIG. 1, lead 115 includes an elongate lead body having a proximal end 117 and a distal end 119. Proximal end 117 is coupled to a connector for connecting to implantable medical device, 105. Distal end 119 is configured for placement in the RV. Lead 115 includes a proximal defibrillation electrode 116, a distal defibrillation electrode 118, and an RV electrode 120. Defibrillation electrode 116 is incorporated into the lead body in a location suitable for supraventricular placement in the RA and/or the superior vena cava. Defibrillation electrode 118 is incorporated into the lead body near distal end 119 for placement in the RV. RV electrode 120 is a pacing-sensing electrode incorporated into the lead body at distal end 119. Electrodes 116, 118, and 120 are each electrically coupled to implantable medical device 105 through a conductor disposed within the lead body. Proximal defibrillation electrode 116, distal defibrillation electrode 118, and the can of implantable medical device 105 allow for delivery of cardioversion/defibrillation pulses to the heart. RV electrode 120 allows for sensing an RV electrogram and delivering pacing pulses to the RV.

Lead 125 is a pacing lead that allows for the atrial signal mapping, either by itself or in combination with leads 110 and/or 115. In one embodiment, as illustrated in FIG. 1, lead 125 is a coronary pacing lead that includes an elongate lead body having a proximal end 121 and a distal end 123. Proximal end 121 is coupled to a connector for connecting to implantable medical device 105. Distal end 123 is configured for placement in the coronary vein. Lead 125 includes an HRA electrode 122, an atrial septal electrode 124, an LA electrode 126, and an LV electrode 128. HRA electrode 122 is a pacing-sensing electrode incorporated into the lead body in a location suitable for placement in the RA or the superior vena cava near the SA node. Atrial septal electrode 124 is incorporated into the lead body in a location suitable for placement in the coronary sinus near the atrial septum. LA electrode 126 is incorporated into the lead body in a location suitable for placement in the coronary sinus or coronary vein near the LA. LV electrode 128 is incorporated into the lead body at the distal end for placement in the coronary vein over the LV. Electrodes 122, 124, 126, and 128 are each electrically coupled to implantable medical device 105 through a conductor disposed within the lead body. HRA electrode 122 allows for sensing an RA electrogram indicative of depolarizations in the upper RA region near the SA node and delivering pacing pulses to that region. Atrial septal electrode 124 allows for sensing an atrial septal electrogram indicative of depolarizations in the atrial septal region and delivering pacing pulses to that region. LA electrode 126 allows for sensing an LA electrogram indicative of depolarizations in the LA and delivering pacing pulses to the LA. LV electrode 128 allows for sensing an LV electrogram indicative of depolarizations in the LV and delivering pacing pulses to the LV. LV electrode 128 is at or near distal end 123. At least a distal portion of the elongate lead body that includes distal end 123 is made suitable for insertion into the coronary vein through the coronary sinus. In one embodiment, HRA electrode 122, atrial septal electrode 124, and LA electrode 126 are each a ring electrode incorporated onto the elongate lead body. The portion of the elongate lead body onto which HRA electrode 122, atrial septal electrode 124, and LA electrode 126 are incorporated has a diameter suitable for insertion into the coronary sinus and a portion of the sinus vein next to the coronary sinus. Atrial septal electrode 124 has an outer diameter suitable for placement in the coronary sinus. LA electrode 126 has an outer diameter suitable for placement in the coronary sinus and the portion of the sinus vein next to the coronary sinus.

In the exemplary embodiment illustrated in FIG. 1, pacing-sensing electrodes 112, 114A, 114B, 120, 122, 124, 126, and 128 each allow for sensing by pairing with another pacing-sensing electrode or the can of implantable medical device 105. In one example, atrial septal electrodes 114A and 114B allow for bipolar sensing of an atrial septal electrogram, while one or more of electrodes 112, 120, 122, 124, 126, and 128 each allow for sensing of an electrogram from wherein the electrode is placed by using a different electrode selected from electrodes 112, 114A, 114B, 120, 122, 124, 126, and 128 as a reference electrode. In another example, atrial septal electrodes 114A and 114B allow for bipolar sensing of an atrial septal electrogram, while one or more of electrodes 112, 120, 122, 124, 126, and 128 each allow for unipolar sensing of an electrogram from wherein the electrode is placed by using the can of implantable medical device 105 as a reference electrode. In other embodiments, one or more of electrodes 112, 120, 122, 124, 126, and 128 are each replaceable by a pair of electrodes allowing for bipolar sensing when preferred. After reading and comprehending this document, those skilled in the art will understand that the present subject matter does not require the inclusion or use of all the electrodes illustrated in FIG. 1. In one embodiment, for example, an HRA electrode, an atrial septal electrode, an LA electrode, and a ventricular electrode are needed for tachyarrhythmia detection and classification according to the present subject matter. The HRA electrode can be either HRA electrode 112 or HRA electrode 122. The atrial septal electrode can include one or more of atrial septal electrodes 114A, 114B, and 124. The ventricular electrode can be either RV electrode 120 or LV electrode 128. Thus, various combinations of leads and electrodes are possible. For example, lead 125 alone, with electrodes 122, 124, 126, and 128, is sufficient for the tachyarrhythmia detection and classification according to the present subject matter. Alternatively, lead 110 with electrodes 112, 114A, and 114B and a modified version of lead 125 with electrodes 126 and 128 are used. Other combinations are suitable based on overall design and implantation considerations as understood by those skilled in the art.

External system 190 allows for programming of implantable medical device 105 and receives signals acquired by implantable medical device 105. In one embodiment, telemetry link 185 is an inductive telemetry link. In an alternative embodiment, telemetry link 185 is a far-field radio-frequency telemetry link. Telemetry link 185 provides for data transmission from implantable medical device 105 to external system 190. This may include, for example, transmitting real-time physiological data acquired by implantable medical device 105, extracting physiological data acquired by and stored in implantable medical device 105, extracting therapy history data stored in implantable medical device 105, and extracting data indicating an operational status of implantable medical device 105 (e.g., battery status and lead impedance). In one embodiment, the classifications of detected tachyarrhythmias and/or the measured inter-atrial interval are transmitted to external system 190, for purposes such as cardiac condition diagnosis and therapy adjustment. Telemetry link 185 also provides for data transmission from external system 190 to implantable medical device 105. This may include, for example, programming implantable medical device 105 to acquire physiological data, programming implantable medical device 105 to perform at least one self-diagnostic test (such as for a device operational status), programming implantable medical device 105 to run a signal analysis algorithm (such as an algorithm implementing the tachyarrhythmia detection and classification method discussed in this document), and programming implantable medical device 105 to deliver pacing and/or cardioversion/defibrillation therapies.

Figure 2:
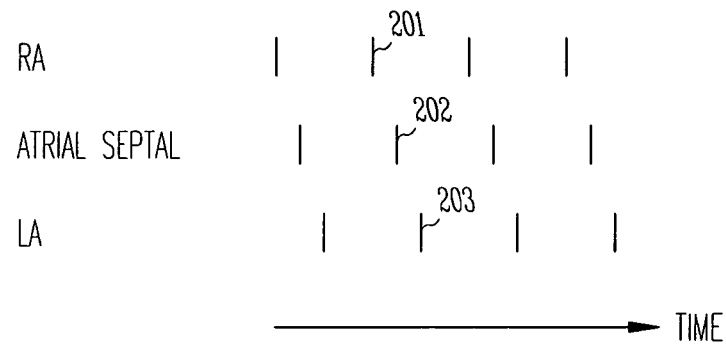
FIG. 2 is a graph illustrating an atrial activation sequence indicating a tachyarrhythmia of RA origin.
Figure 3:
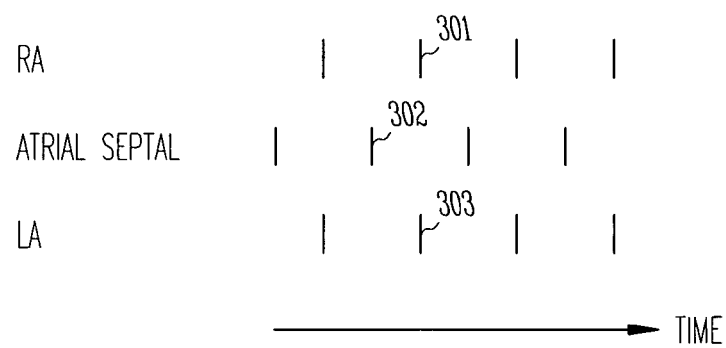
FIG. 3 is a graph illustrating an atrial activation sequence indicating a tachyarrhythmia of atrial septal or ventricular origin.
Figure 4:
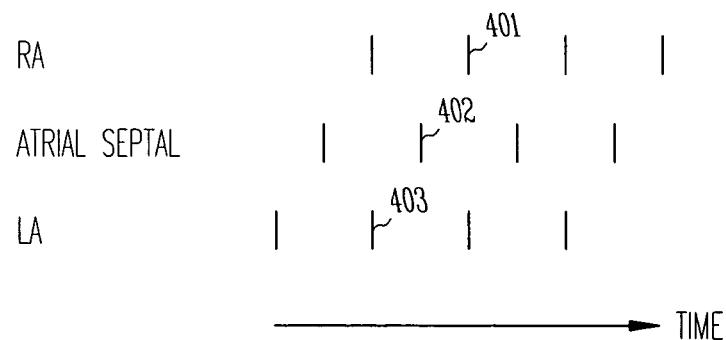
FIG. 4 is a graph illustrating an atrial activation sequence indicating a tachyarrhythmia of LA origin.

FIGS. 2-4 illustrate mapped atrial activation sequences indicating tachyarrhythmias of substantially different origins. In each of FIGS. 2-4, events markers representing regional depolarizations detected from an RA electrogram (sensed by an HRA electrode), an atrial septal electrogram, and an LA electrogram are shown.

FIG. 2 is a graph illustrating an atrial activation sequence indicating a tachyarrhythmia of RA origin (SVT of RA origin). RA event 201, atrial septal event 202, and LA event 203 represent regional depolarizations during an atrial depolarization. That is, events 201, 202, and 203 result from the conduction of the same electrical impulse across the atria. As illustrated in FIG. 2, the atrial activation sequence shows that RA event 201 occurs first during the atrial depolarization and is referred to as an "RA pattern". This indicates that the origin of the electrical impulse (ectopic focus) is most likely in the RA.

FIG. 3 is a graph illustrating an atrial activation sequence indicating a tachyarrhythmia of atrial septal origin or ventricular origin with one-to-one retrograde conduction (SVT of atrial septal origin or VT). RA event 301, atrial septal event 302, and LA event 303 represent regional depolarizations during an atrial depolarization. That is, events 301, 302, and 303 resulted from the conduction of the same electrical impulse across the atria. As illustrated in FIG. 3, the atrial activation sequence shows that atrial septal event 302 occurs first during the atrial depolarization and is referred to as an "atrial septal pattern". This indicates that the origin of the electrical impulse (ectopic focus) is in the atrial septal region in a ventricle. In the case that the ectopic focus is in the ventricle, the electrical impulse, by following a retrograde conduction path, is conducted from the ventricle through the atrioventricular node to the atrial septum and then to other regions of the atria. Thus, the atrial signal mapping shows that the atrial septum depolarizes first.

FIG. 4 is a graph illustrating an atrial activation sequence indicating a tachyarrhythmia of LA origin (SVT of LA origin). RA event 401, atrial septal event 402, and LA event 403 represent regional depolarizations during an atrial depolarization. That is, events 401, 402, and 403 resulted from the conduction of the same electrical impulse across the atria. As illustrated in FIG. 4, the atrial activation sequence shows that LA event 403 occurs first during the atrial depolarization and is referred to as an "LA pattern". This indicates that the origin of the electrical impulse (ectopic focus) is most likely in the LA.

Thus, depending on the location of the ectopic focus, each 1:1 tachyarrhythmia of atrial origin (SVT) is associated with one of the RA, atrial septal, and LA patterns of the atrial activation sequence. A 1:1 tachyarrhythmia of ventricular origin (VT) is associated with the atrial septal pattern of atrial activation sequence. Additional analysis, as discussed below, is needed to discriminate between a tachyarrhythmia of ventricular origin and a tachyarrhythmia of atrial septal origin when the atrial signal mapping results on the atrial septal pattern of the atrial activation sequence.

Figure 5:
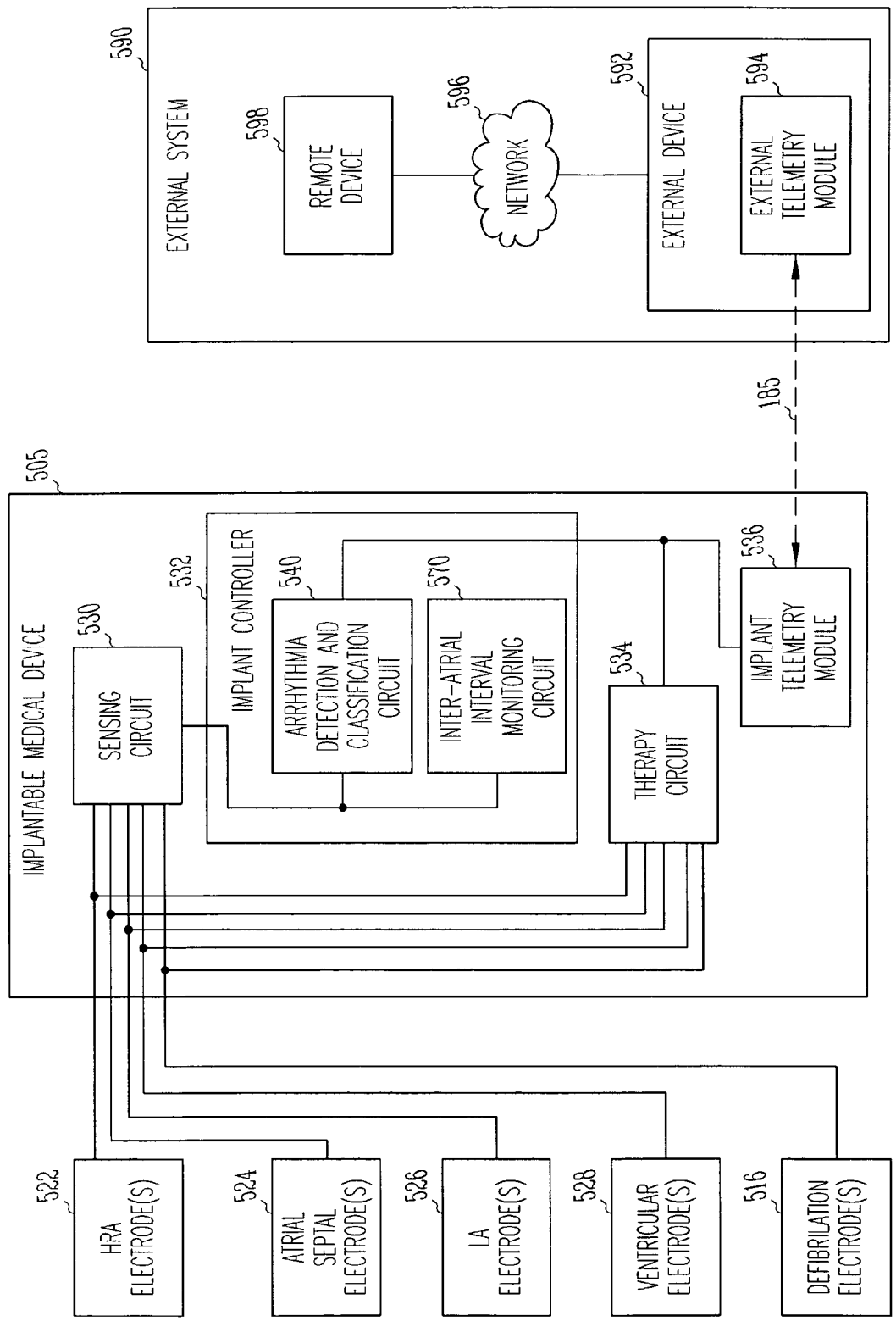
FIG. 5 is a block diagram illustrating an embodiment of portions of a circuit of the CRM system.

FIG. 5 is a block diagram illustrating an embodiment of portions of a circuit of CRM system 100 including HRA electrode(s) 522, atrial septal electrode(s) 524, LA electrode (s) 526, ventricular electrode(s) 528, defibrillation electrode (s) 516, an implantable medical device 505, an external system 590, and telemetry link 185.

HRA electrode(s) 522 allows for sensing of an RA electrogram indicative of regional depolarizations in the region near the SA node. Examples of HRA electrode(s) 522 include HRA electrode(s) 112 and 122 as illustrated in FIG. 1.

Atrial septal electrode(s) 524 allows for sensing of an atrial septal electrogram indicative of regional depolarizations in the atrial septal region. Examples of atrial septal electrode(s) 524 include atrial septal electrodes 114A, 114B, and 124 as illustrated in FIG. 1.

LA electrode(s) 526 allows for sensing of an LA electrogram indicative of regional depolarizations in the LA. Examples of LA electrode(s) 526 include LA electrode 126 as illustrated in FIG. 1.

Ventricular electrode(s) 528 allows for sensing of a ventricular electrogram indicative of regional depolarizations in one of the ventricles. Examples of ventricular electrode(s) 526 include RV electrode 120 and LV electrode 128 as illustrated in FIG. 1.

Defibrillation electrode(s) 516 allows for sensing of electrograms from and delivery of cardioversion/defibrillation pulses to the heart. Examples of defibrillation electrode(s) 528 include defibrillation electrodes 116 and 118 as illustrated in FIG. 1.

In addition to sensing electrograms, HRA electrode(s) 522, atrial septal electrode(s) 524, LA electrode(s) 526, and ventricular electrode(s) 528 also allow for delivery of pacing pulses to the region where they are placed. To sense electrograms using electrode pairs each including two electrodes placed in substantially different regions, HRA electrode(s) 522, atrial septal electrode(s) 524, LA electrode(s) 526, and ventricular electrode(s) 528 each includes one electrode. To sense electrograms using bipolar electrode configurations, HRA electrode(s) 522, atrial septal electrode(s) 524, LA electrode(s) 526, and ventricular electrode(s) 528 each include a pair of electrodes separated by a short distance. A combination of electrode configurations (arrangement of pairs) may be used to achieve desirable electrogram quality.

In one embodiment, HRA electrode(s) 522, atrial septal electrode(s) 524, LA electrode(s) 526, and ventricular electrode(s) 528, each include a pair of electrodes and are individually or collectively programmable for electrogram sensing with various electrode configurations. One or more leads are used to connect the electrodes to implantable medical device 505.

Implantable medical device 505 is one embodiment of implantable medical device 105 and includes a sensing circuit 530, an implant controller 532, a therapy circuit 534, and an implant telemetry module 536. Sensing circuit 530 senses electrograms. Implant controller 532 controls the operation of implantable medical device 505, including processing and analyzing the electrograms and controlling delivery of pacing, cardioversion, and defibrillation pulses. Therapy circuit 534 delivers the pacing, cardioversion, and/ or defibrillation pulses. Implantable telemetry module 536 receives data from, and sends data to, external system 590 via telemetry link 185.

Implant controller 532 includes one or both of an arrhythmia detection and classification circuit 540 and an inter-atrial interval monitoring circuit 570. Arrhythmia detection and classification circuit 540 detects and classifies tachyarrhythmias based on the electrograms sensed through one or more of HRA electrode(s) 522, atrial septal electrode(s) 524, LA electrode(s) 526, ventricular electrode(s) 528, defibrillation electrode(s) 516. Based on the classification of each detected tachyarrhythmia, implant controller 532 determines whether to deliver a therapy, including the type of the therapy and the site to which the therapy is delivered. Therapy circuit 534 delivers therapies in response to command signals received from implant controller 532. Inter-atrial interval monitoring circuit 570 measures an inter-atrial interval from two atrial electrograms, such as an RA electrogram sensed by HRA electrode(s) 522 and an LA electrogram sensed by LA electrode(s) 526. The inter-atrial interval is used as a prognostic factor for monitoring development of, or effect of a therapy on, cardiac conditions such as AF or heart failure. Exemplary embodiments illustrating details of arrhythmia detection and classification circuit 540 and inter-atrial interval monitoring circuit 570 are discussed below.

External system 590 is one embodiment of external system 190 and includes an external telemetry module 594 that receives data from, and transmits data to, implantable medical device 505. In one embodiment, external system 590 includes a programmer. In another embodiment, as illustrated in FIG. 5, external system 590 is a patient management system including an external device 592 in proximity of implantable medical device 505, a remote device 598 in a relatively distant location, and a telecommunication network 596 linking the external device and the remote device. The patient management system allows access to implantable medical device 505 from a remote location, for purposes such as monitoring patient status and adjusting therapies.

Figure 6:
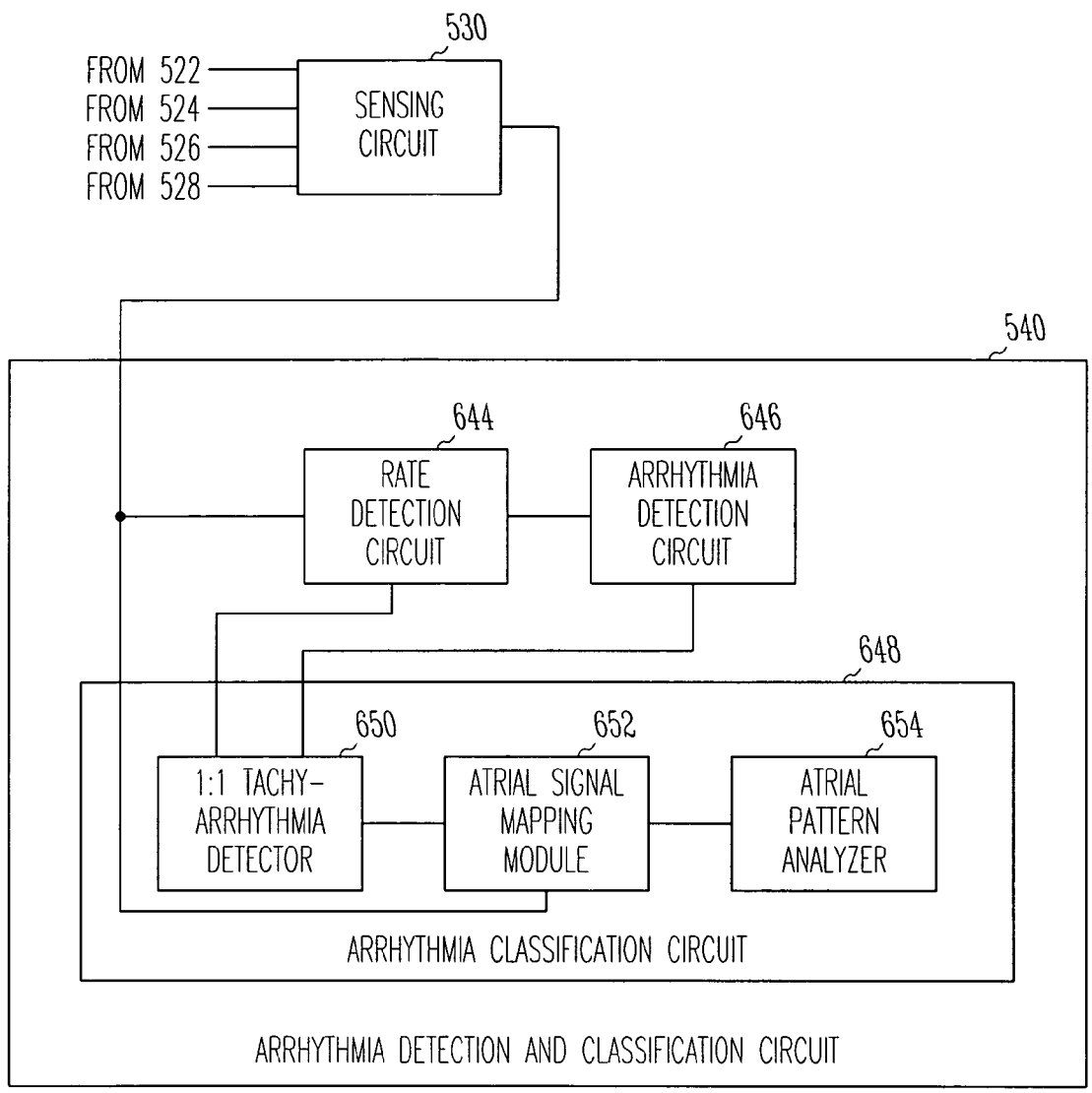
FIG. 6 is a block diagram illustrating an embodiment of the arrhythmia detection and classification circuit.

FIG. 6 is a block diagram illustrating an embodiment of arrhythmia detection and classification circuit 540. Arrhythmia detection and classification circuit 540 is coupled to sensing circuit 530 and includes a rate detection circuit 644, an arrhythmia detection circuit 646, and an arrhythmia classification circuit 648.

Sensing circuit 530 senses a plurality of atrial electrograms (including the RA, atrial septal, and LA electrograms as discussed above) and at least one ventricular electrogram (the RV or LV electrogram as discussed above) through electrodes 522, 524, 526, and 528. Rate detection circuit 644 detects an atrial rate from at least one of the RA, atrial septal, and LA electrograms and a ventricular rate from the RV or LV electrogram. Arrhythmia detection circuit 646 detects a tachyarrhythmia based on at least one of the atrial rate and the ventricular rate. In one embodiment, arrhythmia detection circuit 646 indicates a detection of tachyarrhythmia when the ventricular rate exceeds a predetermined tachyarrhythmia threshold rate.

Arrhythmia classification circuit 648 includes a 1:1 tachyarrhythmia detector 650, an atrial signal mapping module 652, and an atrial pattern analyzer 654. A detected tachyarrhythmia is classified by 1:1 tachyarrhythmia detector 648 as a 1:1 tachyarrhythmia when the atrial rate and the ventricular rate are substantially equal. In one embodiment, 1:1 tachyarrhythmia detector 648 classifies the detected tachyarrhythmia as a 1:1 tachyarrhythmia when the difference between the atrial rate and the ventricular rate is within 10 beats per minute. Atrial signal mapping module 652 maps an atrial activation sequence based on the RA, atrial septal, and LA electrograms. The atrial activation sequence indicative of an order of regional depolarizations in the RA region near the SA node, the atrial septal region, and the LA during an atrial depolarization. Atrial pattern analyzer 654 classifies the 1:1 tachyarrhythmia by its origin based on the atrial activation sequence.

Arrhythmia classification circuit 648 also includes a circuit for classifying the detected tachyarrhythmia when the atrial rate and the ventricular rate are not substantially equal. In one embodiment, this circuit classifies the detected tachyarrhythmia as a VT if the atrial rate is substantially lower than the ventricular rate and as a SVT or a dual arrhythmia if the atrial rate is substantially higher than the ventricular rate. A further detection is performed to discriminate between SVT and dual arrhythmia.

Figure 7:
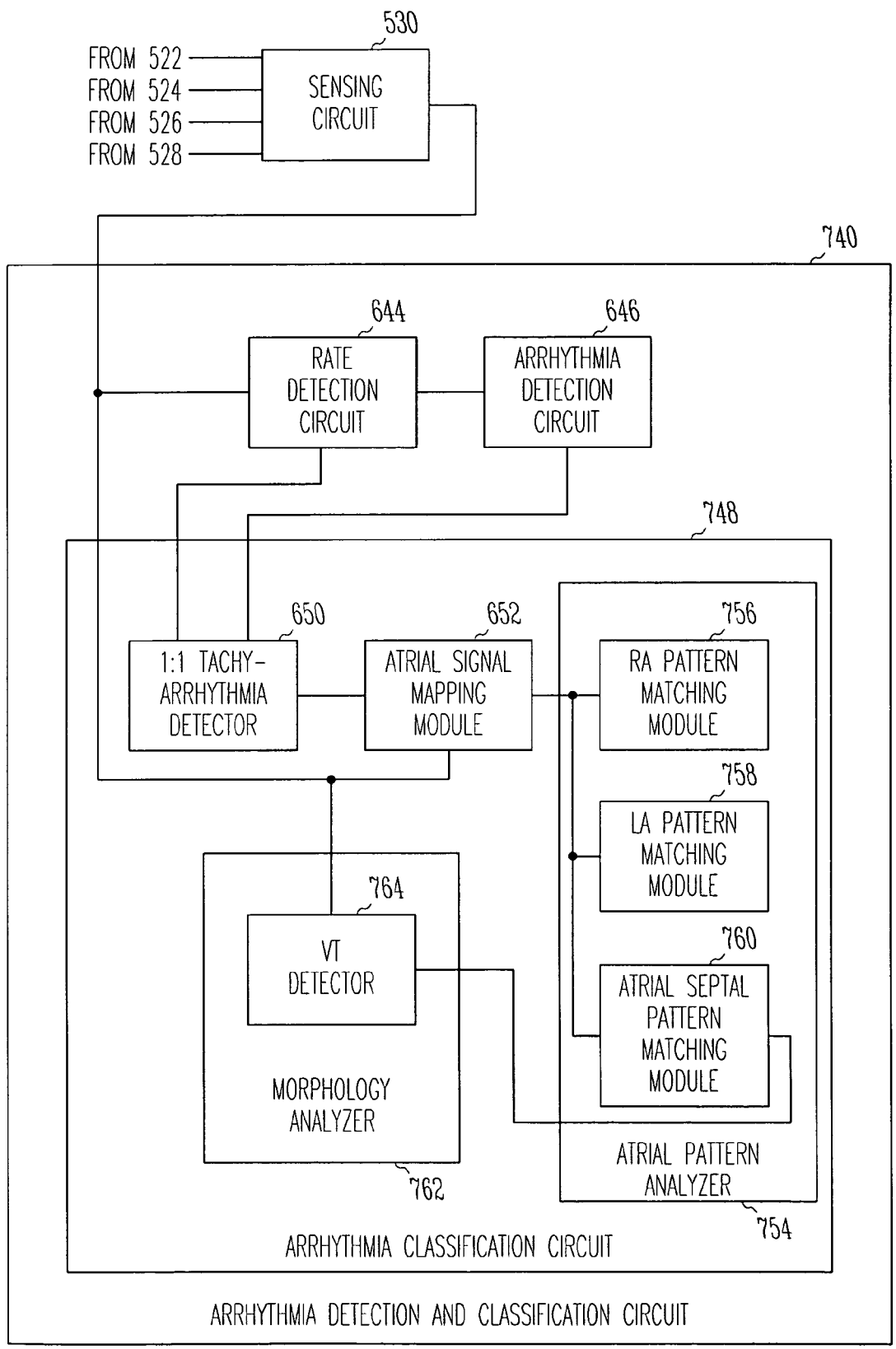
FIG. 7 is a block diagram illustrating a specific embodiment of the arrhythmia detection and classification circuit.

FIG. 7 is a block diagram illustrating an arrhythmia detection and classification circuit 740, which is a specific embodiment of arrhythmia detection and classification circuit 540. Arrhythmia detection and classification circuit 740 is coupled to sensing circuit 530 and includes rate detection circuit 644, arrhythmia detection circuit 646, and an arrhythmia classification circuit 748. Arrhythmia classification circuit 748 is one specific embodiment of arrhythmia classification circuit 648 and includes 1:1 tachyarrhythmia detector 650, an atrial signal mapping module 652, an atrial pattern analyzer 754, and a morphology analyzer 762. Atrial pattern analyzer 754 and morphology analyzer 762 classify the 1:1 tachyarrhythmia by its origin.

Atrial pattern analyzer 754 includes an RA pattern matching module 756, an LA pattern matching module 758, and an atrial septal pattern matching module 760. RA pattern matching module 756 detects an SVT of RA origin by comparing the atrial activation sequence to a predetermined RA pattern template sequence. In one embodiment, RA pattern matching module 756 detects an SVT of RA origin when the first event in the atrial activation sequence is an RA event. LA pattern matching module 758 detects an SVT of LA origin by comparing the atrial activation sequence to a predetermined LA pattern template sequence. In one embodiment, LA pattern matching module 758 detects an SVT of LA origin when the first event in the atrial activation sequence is an LA event. Atrial septal pattern matching module 760 detects one of an SVT of atrial septal origin and a VT by comparing the atrial activation sequence to a predetermined atrial septal pattern template sequence. In one embodiment, atrial septal pattern matching module 760 detects an SVT of atrial septal origin or a VT when the first event in the atrial activation sequence is an RA event. That is, if the atrial activation sequence has the atrial septal pattern, the detected 1:1 tachyarrhythmia is either an SVT of atrial septal origin or a VT. In an alternative embodiment, only two of the RA pattern matching module 756, LA pattern matching module 758, and atrial septal pattern matching module 760 are included because if the atrial activation sequence matches the template sequence of neither pattern, the remaining pattern is identified.

Morphology analyzer 762 further classifies the 1:1 tachyarrhythmia as either an SVT of atrial septal origin or a VT based on morphological features of one or more signals selected from the RA, atrial septal, LA, and ventricular electrograms. In one embodiment, morphology analyzer 762 includes a VT detector 764 that discriminates a VT from an SVT of atrial septal origin by comparing the morphological features to a set of predetermined VT template morphological features. An example of a morphology-based classification of VT and SVT is discussed in U.S. Pat. No. 6,728,572, "SYSTEM AND METHOD FOR CLASSIFYING CARDIAC COMPLEXES," assigned to Cardiac Pacemakers, Inc., which is hereby incorporated by reference in its entirety.

Figure 8:
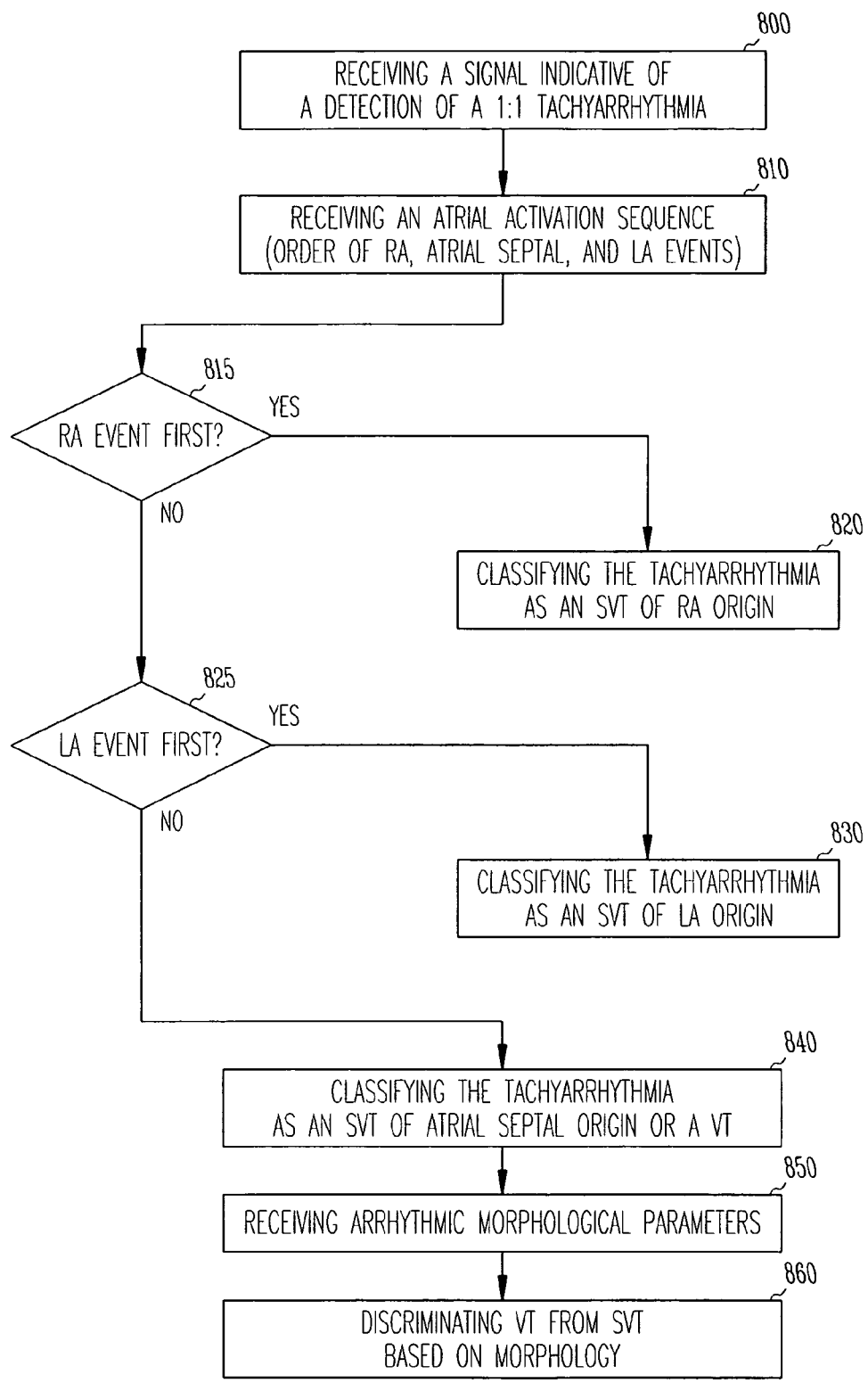
FIG. 8 is a flow chart illustrating an embodiment of a method for classifying tachyarrhythmia based on the atrial signal mapping.

FIG. 8 is a flow chart illustrating an embodiment of a method for classifying tachyarrhythmia based on the atrial signal mapping. The method is applied to classify a 1:1 tachyarrhythmia by its origin. In one embodiment, the method is performed by atrial pattern analyzer 754 and morphology analyzer 762.

A signal indicative of a detection of a 1:1 tachyarrhythmia is received at 800. This starts the process of classifying the detected 1:1 tachyarrhythmia. An atrial activation sequence is received at 810. The atrial activations sequence is the result of the atrial signal mapping and indicates an order of occurrence of an RA event, an atrial septal event, and an LA event during an atrial depolarization. The RA event (also referred to as the HRA event) represents a depolarization indicated by an RA electrogram sensed in the RA region near the SA node. The atrial septal event represents a depolarization indicated by an atrial septal electrogram sensed in the atrial septal region. The LA event represents a depolarization indicated by an LA electrogram sensed near the LA. If the RA event is found to occur first in the atrial activation sequence at 815, the tachyarrhythmia is classified as an SVT of RA origin at 820. If the LA event is found to occur first in the atrial activation sequence at 825, the tachyarrhythmia is classified as an SVT of LA origin at 830. If neither the RA event nor the LA event is found to occur first in the atrial activation sequence, the tachyarrhythmia is classified as an SVT of atrial septal or a VT at 840.

Arrhythmia morphological parameters are received at 850 if the tachyarrhythmia is classified as an SVT of atrial septal or a VT. The arrhythmia morphological parameters the measured from one or more cardiac signals selected from the RA, atrial septal, and LA electrograms and one or more ventricular electrograms sensed during the tachyarrhythmia. The tachyarrhythmia is classified by discriminating a VT from an SVT of atrial septal origin at 860. In one embodiment, the tachyarrhythmia is classified as a VT if the arrhythmia morphological parameters match template VT morphological parameters. The template VT morphological parameters are measured from the one or more cardiac signals during a known VT episode. An example of a method for classifying VT and SVT based on morphology is discussed in U.S. Pat. No. 6,728,572.

Figure 9:
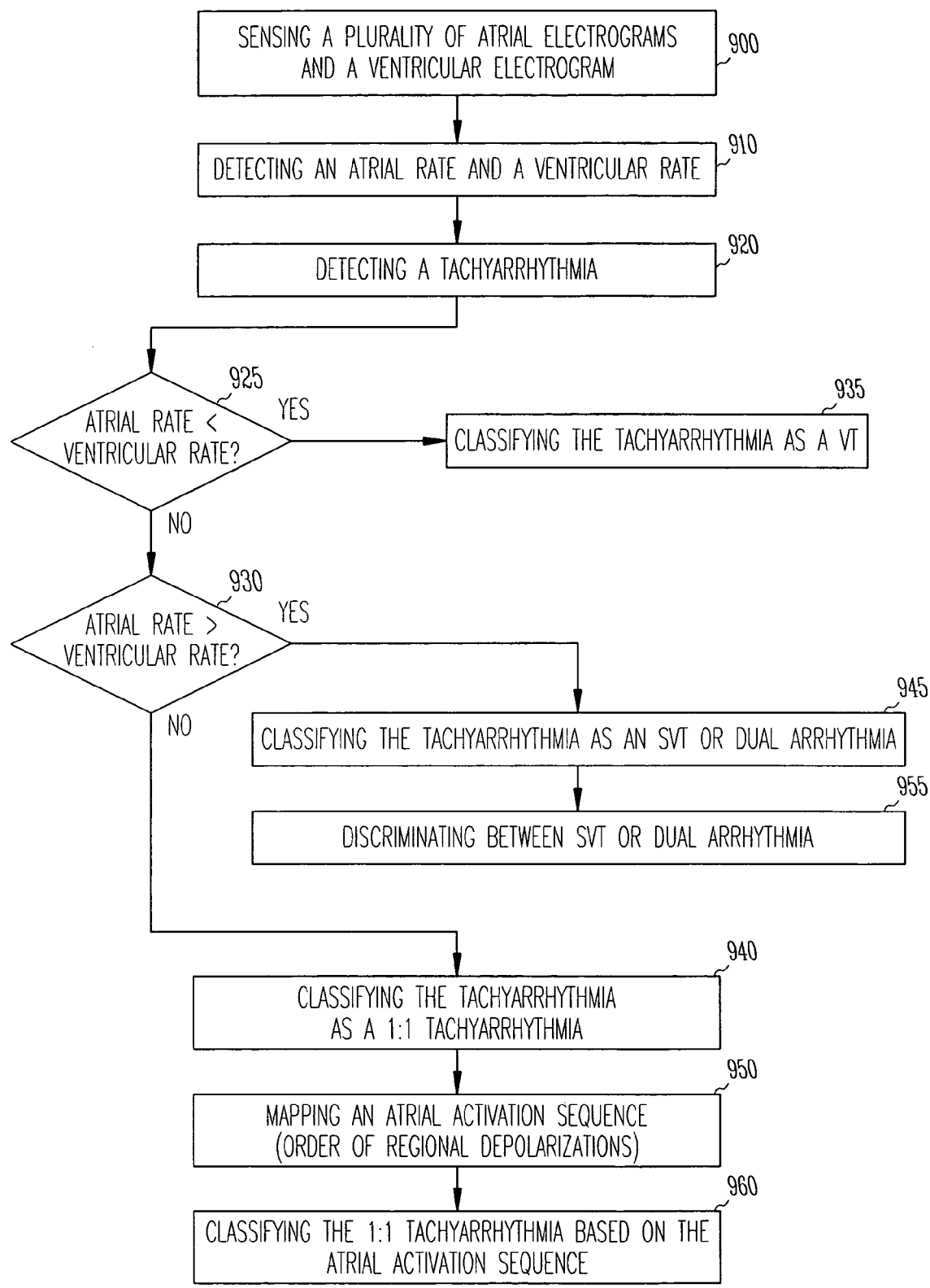
FIG. 9 is a flow chart illustrating an embodiment of a method for detecting and classifying tachyarrhythmia.

FIG. 9 is a flow chart illustrating an embodiment of a method for detecting and classifying tachyarrhythmia. In one embodiment, the method is performed by arrhythmia detection and classification circuit 540 or 740.

A plurality of atrial electrograms from substantially different atrial locations and at least one ventricular electrogram are sensed at 900. In one embodiment, the electrograms include the RA, atrial septal, LA, and ventricular electrograms as discussed above with reference to FIG. 8. An atrial rate and a ventricular rate are detected at 910. The atrial rate is detected from one of the RA, atrial septal, and LA electrograms. The ventricular rate is detected from the ventricular electrogram. A tachyarrhythmia is detected based on at least one of the atrial rate and the ventricular rate at 920. In one embodiment, the tachyarrhythmia is detected when the ventricular rate exceeds a predetermined tachyarrhythmia threshold rate. In one specific embodiment, the tachyarrhythmia threshold rate is programmable in the range between 90 beats per minute and 220 beats per minute.

After being detected, the tachyarrhythmia is classified based on a comparison between the atrial rate and the ventricular rate. If the atrial rate is substantially lower than the ventricular rate at 925, the tachyarrhythmia is classified as a VT at 935. In one embodiment, the tachyarrhythmia is classified as a VT if the atrial rate is lower than the ventricular rate by at least a predetermined margin. In one specific embodiment, the predetermined margin is about 10 beats per minute. If the atrial rate is substantially higher than the ventricular rate at 930, the tachyarrhythmia is classified as a SVT or a dual arrhythmia at 945. In one embodiment, the tachyarrhythmia is classified as a SVT or a dual arrhythmia if the atrial rate is higher than the ventricular rate by at least a predetermined margin. In one specific embodiment, the predetermined margin is about 10 beats per minute. In one embodiment, a farther detection is performed to discriminate between SVT and dual arrhythmia at 955. The result of this further detection determines whether the tachycardia is classified as a SVT or a VT. If the atrial rate is neither substantially lower nor substantially higher than the ventricular rate, the tachyarrhythmia is classified as a 1:1 tachyarrhythmia at 940. In one embodiment, the tachyarrhythmia is classified as a 1:1 tachyarrhythmia if the atrial rate is neither lower than the ventricular rate by a predetermined margin nor higher than the ventricular rate by another predetermined margin. That is, the tachyarrhythmia is classified as a 1:1 tachyarrhythmia if the difference between the atrial rate and the ventricular rate falls within a predetermined window. In one specific embodiment, both predetermined margins are about 10 beats per minute.

After the tachyarrhythmia is classified as a 1:1 tachyarrhythmia at 940, the atrial activation sequence is mapped at 950. As discussed above with reference to FIG. 8, the atrial activation sequence indicates of an order of occurrence of the RA, atrial septal, and LA electrograms during one cardiac cycle. The 1:1 tachyarrhythmia is classified by its origin based on the atrial activation sequence at 960. In one embodiment, the classification process includes steps 810 through 860 as discussed above with reference to FIG. 8.

In one embodiment, the classification of the 1:1 tachyarrhythmia is used to determine whether a therapy is to be delivered, the site to which the therapy is to be delivered, and/or the type of the therapy to be delivered. In one specific embodiment, a ventricular defibrillation pulse is delivered when the 1:1 tachyarrhythmia is classified as a VT. In another embodiment, the classification of the 1:1 tachyarrhythmia and the atrial activation sequence are used for diagnosing and/or monitoring a patient's cardiac conditions.

Figure 10:
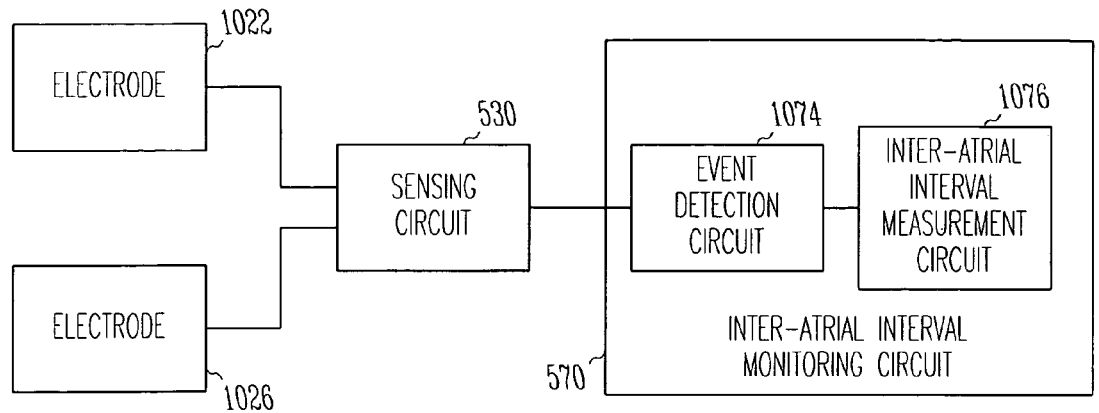
FIG. 10 is a block diagram illustrating an embodiment of the inter-atrial interval monitoring circuit.

FIG. 10 is a block diagram illustrating an embodiment of inter-atrial interval monitoring circuit 570. Inter-atrial interval monitoring circuit 570 is coupled to sensing circuit 530 and includes an event detection circuit 1074 and an inter-atrial interval measurement circuit 1076. Sensing circuit 530 senses an RA electrogram through electrode 1022 and an LA electrogram through electrode 1026. In one embodiment, electrode 1022 is placed in the RA or superior vena cava near the SA node, and electrode 1026 is placed in the coronary sinus or coronary vein near the LA. In one embodiment, electrodes 1022 and 1026 are incorporated into a single lead coupled to sensing circuit 530. In another embodiment, electrodes 1022 and 1026 are incorporated into separate leads coupled to sensing circuit 530. Event detection circuit 1074 detects an RA event from the RA electrogram and an LA event from the LA electrogram for each atrial depolarization. Inter-atrial interval measurement circuit 1076 measures an inter-atrial interval, which is a time interval between the RA event and the LA event during one atrial depolarization.

Figure 11:
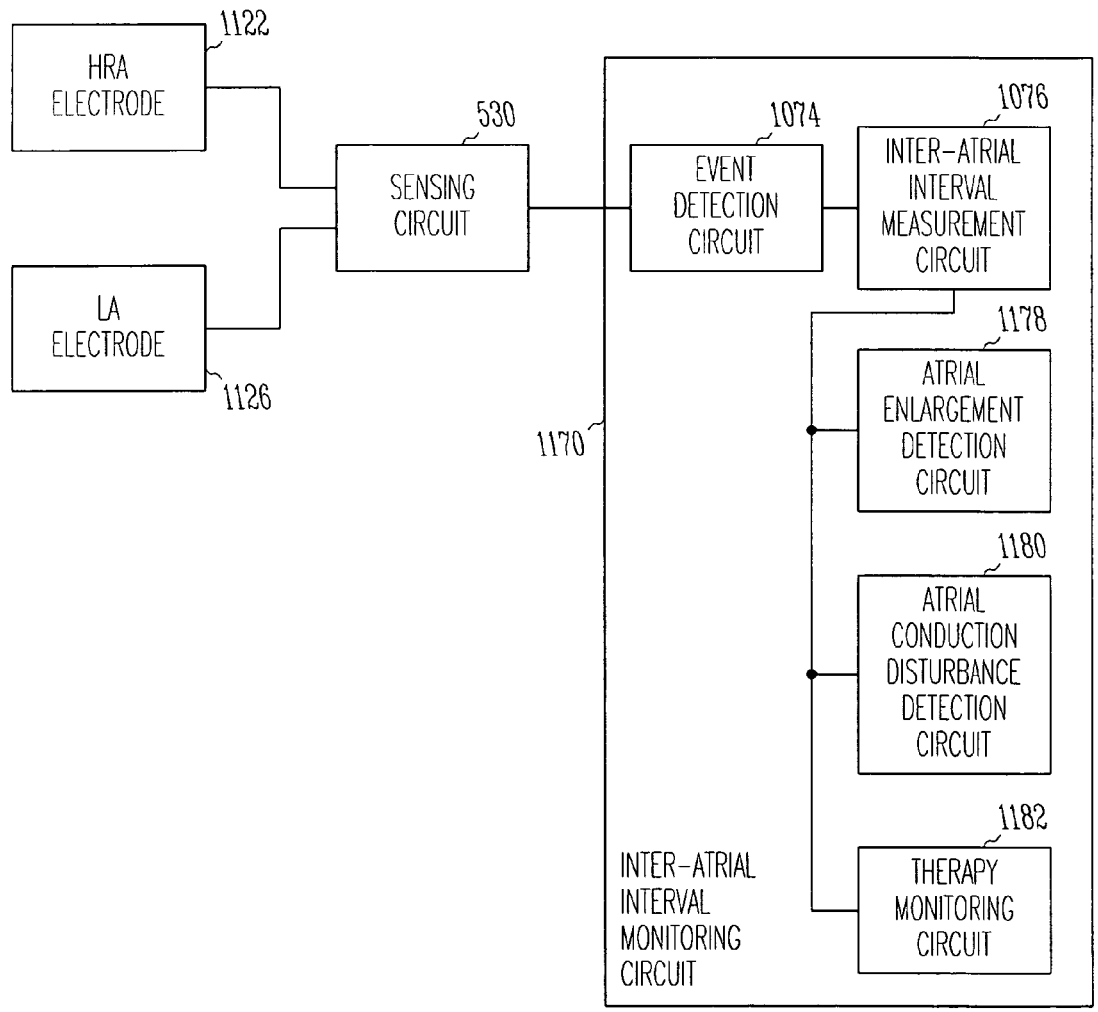
FIG. 11 is a block diagram illustrating a specific embodiment of the inter-atrial interval monitoring circuit.

FIG. 11 is a block diagram illustrating inter-atrial interval monitoring circuit 1170, which is a specific embodiment of the inter-atrial interval monitoring circuit. Inter-atrial interval monitoring circuit 1170 is coupled to sensing circuit 530 and includes event detection circuit 1074, inter-atrial interval measurement circuit 1076, an atrial enlargement detection circuit 1178, an atrial conduction disturbance detection circuit 1180, and a therapy monitoring circuit 1182. Sensing circuit 530 senses an RA electrogram through an HRA electrode 1122 and an LA electrogram through an LA electrode 1126. Examples of HRA electrode 1122 include HRA electrodes 112 and 122. Example of LA electrode includes LA electrode 126.

The inter-atrial interval is reflected in the duration of the P-wave in a surface ECG. A normal range of the P-wave duration is known to be between 80-120 milliseconds. In one embodiment, inter-atrial interval monitoring circuit 1170 eliminates the need of measuring the P-wave duration using a surface ECG. This allows, for example, the monitoring of development of AF and/or heart failure from a distant location using external system 590 as illustrated in FIG. 5. AF is known to be associated with atrial enlargement and atrial conduction disturbance. Heart failure is usually associated with enlargement of the LA.

Atrial enlargement detection circuit 1178 detects an abnormal enlargement of at least one atrium based on the inter-atrial interval. In one embodiment, atrial enlargement detection circuit 1178 includes a comparator that has an input to receive the inter-atrial interval, another input to receive a predetermined threshold interval, and an output to indicate an abnormal enlargement of at least one atrium when the inter-atrial interval exceeds the predetermined threshold interval. In one embodiment, implant controller 532 starts delivering a therapy in response to the indication of the abnormal enlargement. In another embodiment, implant controller 532 produces an alert signal in response to the indication of the abnormal enlargement. The alert signal is transmitted to external system 590 via telemetry link 185.

Atrial conduction disturbance detection circuit 1180 detects a variance of the inter-atrial interval indicating the degree of atrial conduction disturbance. In one embodiment, atrial conduction disturbance detection circuit 1180 includes a variance calculation module and a comparator. The variance calculation module calculates a variance of the inter-atrial interval, which is the difference between successive inter-atrial intervals averaged for a predetermined period of time or predetermined number of heart beats. The comparator includes an input to receive the variance of the inter-atrial interval, another input to receive a predetermined threshold variance, and an output to indicate an atrial conduction disturbance when the variance of the inter-atrial interval exceeds the predetermined threshold variance. In one embodiment, implant controller 532 starts delivering a therapy in response to the indication of the atrial conduction disturbance. In another embodiment, implant controller 532 produces an alert signal in response to the indication of the atrial conduction disturbance. The alert signal is transmitted to external system 590 via telemetry link 185.

Therapy monitoring circuit 1182 monitors the effect of one or more therapies based on the inter-atrial interval. In one embodiment, pacing and/or drug therapies are delivered to prevent or treat AF and/or heart failure. The therapies are indicated as being effective when the inter-atrial interval decreases toward its normal range and/or when the degree of atrial conduction disturbance is reduced or minimized. In one embodiment, therapy monitoring circuit 1182 allows for adjustment or optimization of therapy parameters based on the inter-atrial interval and/or the variance in the inter-atrial interval. One or more therapy parameters are selected for reduced or minimized inter-atrial interval and/or reduced or minimized variance in the inter-atrial interval.

Figure 12:
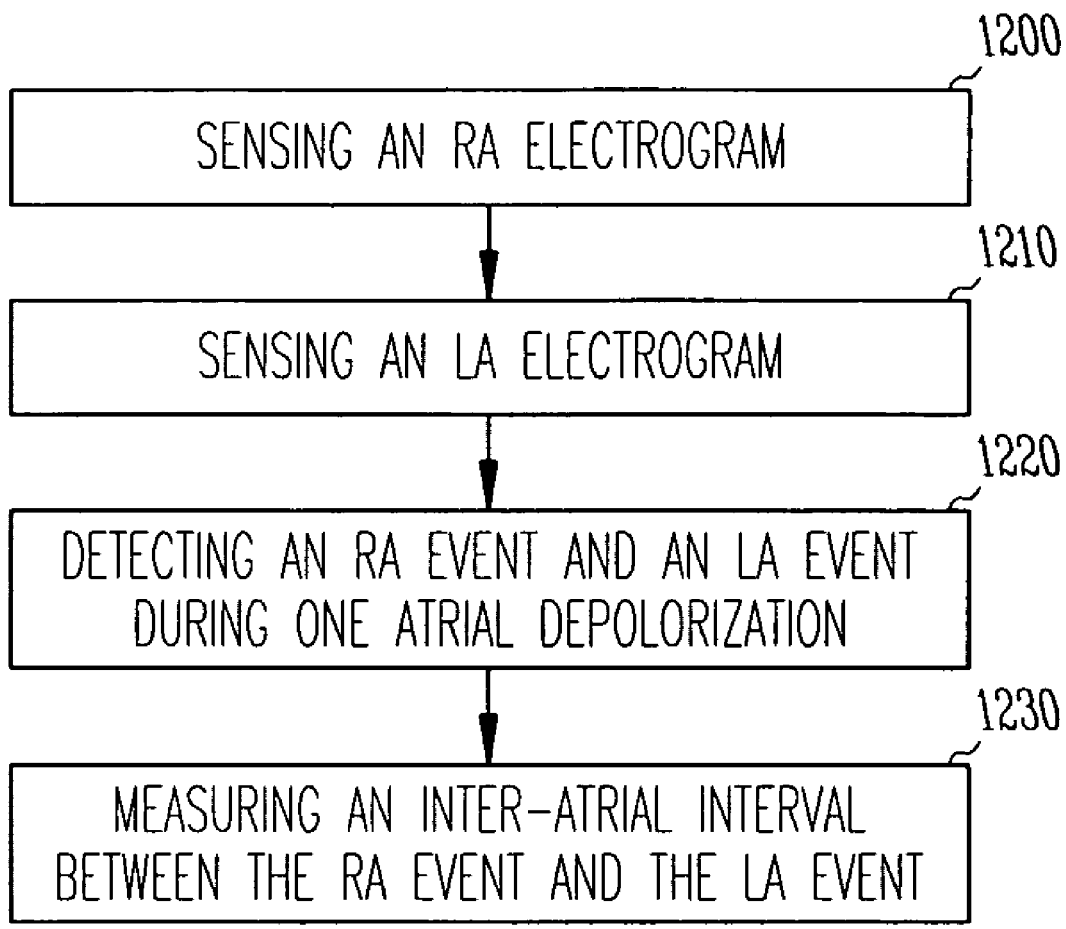
FIG. 12 is a flow chart illustrating an embodiment of a method for monitoring cardiac conditions based on an inter-atrial interval.

FIG. 12 is a flow chart illustrating an embodiment of a method for monitoring cardiac conditions based on an inter-atrial interval. In one embodiment, the method is performed by inter-atrial interval monitoring circuit 570 or 1170.

An RA electrogram is sensed using an electrode placed in the RA or the superior vena cava near the SA node at 1200. An LA electrogram is sensed using an electrode placed in the coronary sinus or coronary vein near the LA at 1210. An RA event is detected from the RA electrogram, and an LA event is detected from the LA electrogram, for each atrial depolarization, at 1220. The inter-atrial interval is measured as the time interval between the RA event and the LA event during one atrial depolarization at 1230.

In one embodiment, the measured inter-atrial interval is used to monitor the development of AF and/or heart failure. In one embodiment, an abnormal enlargement of at least one atrium is detected based on the inter-atrial interval. The abnormal enlargement is detected when the inter-atrial interval exceeds a predetermined threshold interval. The detection of the abnormal enlargement is used to initiate and/or to monitor a therapy. In another embodiment, atrial conduction disturbance is detected based on the variance of the inter-atrial interval. A variance of the inter-atrial interval is measured to indicate the degree of atrial disturbance. The atrial conduction disturbance is detected when the variance of the inter-atrial interval exceeds a predetermined threshold variance. The detection of the atrial conduction disturbance is used to initiate and/or to monitor a therapy.

It is to be understood that the above detailed description is intended to be illustrative, and not restrictive. For example, the atrial signal mapping-based tachyarrhythmia classification can be combined with other methods of tachyarrhythmia classification for enhance the accuracy of classification of 1:1 tachyarrhythmias. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management system coupled to a heart having a right atrium (RA) connected to a superior vena cava, a left atrium (LA), a left ventricle (LV), a sinoatrial (SA) node, an atrial septum, a coronary sinus, and a coronary vein, the system comprising:

a high RA (HRA) electrode configured for placement near the SA node to sense an RA electrogram;

an LA electrode configured for placement near the LA to sense an LA electrogram;

an atrial septal electrode configured for placement in or near the atrial septum to sense an atrial septal electrogram;

a ventricular electrode configured for placement in or near a ventricle to sense a ventricular electrogram; and an implantable medical device coupled to the HRA electrode, the LA electrode, the atrial septal electrode, and the ventricular electrode, the implantable medical device including a sensing circuit to sense the RA electrogram, the LA electrogram, the atrial septal electrogram, and the ventricular electrogram, an arrhythmia detection circuit to detect a tachyarrhythmia based in at least one of the RA electrogram, the LA electrogram, the atrial septal electrogram, and the ventricular electrogram, and an arrhythmia classification circuit to classify the detected tachyarrhythmia, the arrhythmia classification circuit including:

an atrial signal mapping module configured to map an atrial activation sequence using the RA electrogram, the LA electrogram, and the atrial septal electrogram, the atrial activation sequence indicative of an order of regional depolarizations during an atrial depolarization; and an atrial pattern analyzer configured to classify the detected tachyarrhythmia using the atrial activation sequence.

2. The system of claim 1, wherein the implantable medical device further comprises:

an event detection circuit, coupled to the sensing circuit, to detect an RA event from the RA electrogram and an LA event from the LA electrogram during an atrial depolarization; and an inter-atrial interval measurement circuit, coupled to the event detection circuit, to measure a time interval between the RA event and the LA event.

3. The system of claim 1, further comprising a first lead including the HRA electrode, the LA electrode, and the atrial septal electrode, and wherein the HRA electrode is configured for placement in the RA or the superior vena cava near the SA node, the LA electrode is configured for placement in the coronary sinus or the coronary vein near the LA, and the atrial septal electrode is configured for placement in the coronary sinus near the atrial septum.

4. The system of claim 3, wherein the first lead further comprises an LV electrode configured for placement in the coronary vein over the LV to sense an LV electrogram.

5. The system of claim 4, wherein the atrial pattern analyzer is configured to classify the tachyarrhythmia using the atrial activation sequence and the LV electrogram.

6. A system of claim 1, further comprising a first lead including at least the HRA electrode and a second lead including at least the LA electrode, and wherein the HRA electrode is configured for placement in the RA or the superior vena cava near the SA node, and the LA electrode is configured for placement in the coronary sinus or the coronary vein near the LA.

7. The system of claim 6, wherein the first lead further comprises the atrial septal electrode, and wherein the atrial septal electrode is configured for placement in the RA in or near the atrial septum.

8. The system of claim 6, wherein the second lead further comprises the atrial septal electrode, and wherein the atrial septal electrode is configured for placement in the coronary sinus near the atrial septum.

9. The system of claim 1, wherein the atrial pattern analyzer is configured to classify the tachyarrhythmia using the atrial activation sequence and the ventricular electrogram.

10. The system of claim 1, further comprising an external system communicatively coupled to the implantable medical device.

11. The system of claim 10, wherein the external system comprises an external device communicatively coupled to the implantable medical device via telemetry.

12. The system of claim 11, wherein the external system further comprises:
 a telecommunication network coupled to the external device; and
 a remote device coupled to the telecommunication network.

13. A system for tachyarrhythmia detection and classification, the system comprising:
 a sensing circuit to sense a plurality of atrial electrograms and at least one ventricular electrogram;
 a rate detection circuit, coupled to the sensing circuit, to detect an atrial rate from at least one atrial electrogram of the plurality of atrial electrograms and a ventricular rate from the at least one ventricular electrogram;
 an arrhythmia detection circuit, coupled to the rate detection circuit, to detect a tachyarrhythmia using at least one of the atrial rate and the ventricular rate; and
 an arrhythmia classification circuit coupled to the sensing circuit, the rate detection circuit, and the arrhythmia detection circuit, the arrhythmia classification circuit including:
  a 1:1 tachyarrhythmia detector adapted configured to classify the detected tachyarrhythmia as a 1:1 tachyarrhythmia when the atrial rate and the ventricular rate are substantially equal;
  an atrial signal mapping module configured to map an atrial activation sequence using the plurality of atrial electrograms, the atrial activation sequence indicative of an order of regional depolarizations during an atrial depolarization; and
  an atrial pattern analyzer configured to classify the 1:1 tachyarrhythmia using the atrial activation sequence.

14. The system of claim 13, wherein the atrial pattern analyzer comprises at least two of:
 a right atrial pattern matching module to detect a supraventricular tachyarrhythmia of a right atrial origin by comparing the atrial activation sequence to a predetermined right atrial pattern template sequence;
 a left atrial pattern matching module to detect an supraventricular tachyarrhythmia of a left atrial origin by comparing the atrial activation sequence to a predetermined left atrial pattern template sequence; and
 an atrial septal pattern matching module to detect one of a supraventricular tachyarrhythmia of atrial septal origin and a ventricular tachyarrhythmia by comparing the atrial activation sequence to a predetermined atrial septal pattern template sequence.

15. The system of claim 13, wherein the arrhythmia classification circuit further comprises a morphology analyzer, coupled to the atrial pattern analyzer, to further classify the 1:1 tachyarrhythmia using morphological features of one or more signals selected from the plurality of atrial electrogram and the at least one ventricular electrogram.

16. The system of claim 15, wherein the morphology analyzer further comprises a ventricular tachyarrhythmia detector to discriminate a ventricular tachyarrhythmia from a supraventricular tachyarrhythmia of atrial septal origin by comparing the morphological features to a set of predetermined ventricular tachyarrhythmia template morphological features.

17. The system of claim 13, further comprising a plurality of electrodes and one or more leads coupled to the sensing circuit, the plurality of electrodes incorporated into the one or more leads and including:
 a right atrial electrode configured to sense a right atrial electrogram;
 a left atrial electrode configured to sense a left atrial electrogram;
 an atrial septal electrode configured to sense an atrial septal electrogram; and
 a ventricular electrode configured to sense the ventricular electrogram.

18. The system of claim 17, wherein the one or more leads comprise one lead including the right atrial electrode, the left atrial electrode, the atrial septal electrode, and the ventricular electrode.

19. The system of claim 17, wherein the one or more leads comprises a first lead including at least the right atrial electrode and a second lead including at least the left atrial electrode.

20. A system, coupled to a heart having a right atrium (RA) connected to a superior vena cava, a left atrium (LA), a sinoatrial (SA) node, a coronary sinus, and a coronary vein, for monitoring prognostic factors for atrial fibrillation and heart failure, the system comprising:
 a first electrode configured for placement in the RA or superior vena cava near the SA node to sense an RA electrogram indicative of cardiac depolarizations in an upper RA region including the SA node;
 a second electrode configured for placement in the coronary sinus or coronary vein near the LA to sense an LA electrogram indicative of cardiac depolarizations in the LA;
 a sensing circuit coupled to the first electrode to sense the RA electrogram and coupled to the second electrode to sense the LA electrogram; and
 an inter-atrial interval monitoring circuit configured to detect one or more of atrial enlargement and atrial conduction disturbance using an inter-atrial interval, the inter-atrial interval monitoring circuit including:
  an event detection circuit, coupled to the sensing circuit, to detect an RA event from the RA electrogram and an LA event from the LA electrogram during an atrial depolarization; and
  an inter-atrial interval measurement circuit, coupled to the event detection circuit, to measure the inter-atrial interval being a time interval between the RA event and the LA event.

21. The system of claim 20, further including a first lead coupled to the sensing circuit, wherein the first electrode and the second electrode are incorporated into the first lead.

22. The system of claim 20, further including a first lead coupled to the sensing circuit and a second lead coupled to the sensing circuit, wherein the first electrode is incorporated into the first lead, and the second electrode is incorporated into the second lead.

23. The system of claim 20, wherein the inter-atrial interval monitoring circuit comprises an atrial enlargement detection circuit coupled to the inter-atrial interval measurement circuit, the atrial enlargement detection circuit configured to detect an abnormal enlargement of at least one atrium using the inter-atrial interval.

24. The system of claim 23, wherein the atrial enlargement detection circuit comprises a comparator including a first input to receive the inter-atrial interval, a second input to receive a predetermined threshold interval, and an output to indicate the abnormal enlargement of at least one atrium when the inter-atrial interval exceeds the predetermined threshold interval.

25. The system of claim 20, wherein the inter-atrial interval monitoring circuit comprises an atrial conduction disturbance detection circuit coupled to the inter-atrial interval measurement circuit, the atrial conduction disturbance detection circuit configured to detect a variance of the inter-atrial interval.

26. The system of claim 25, wherein the atrial conduction disturbance detection circuit comprises a comparator including a first input to receive the variance of the inter-atrial interval, a second input to receive a predetermined threshold variance, and an output to indicate the atrial conduction disturbance when the variance of the inter-atrial interval exceeds the predetermined threshold variance.

27. The system of claim 20, wherein the inter-atrial interval monitoring circuit comprises a therapy monitoring circuit to monitor an effect of a therapy using the inter-atrial interval.

28. A method for classifying a tachyarrhythmia by origin, comprising:
    receiving an atrial activation sequence indicative of an order of occurrence of a right atrial (RA) event, an atrial septal event, and an left atrial (LA) event during an atrial depolarization;
    classifying the tachyarrhythmia as a tachyarrhythmia of RA origin if the RA event occurs first in the atrial activation sequence;
    classifying the tachyarrhythmia as a tachyarrhythmia of LA origin if the LA event occurs first in the atrial activation sequence; and
    classifying the tachyarrhythmia as a tachyarrhythmia of atrial septal or ventricular origin if the atrial septal event occurs first in the atrial activation sequence.

29. The method of claim 28, further comprising:
    receiving arrhythmic morphological parameters measured from one or more cardiac signals indicative of the tachyarrhythmia; and
    classifying the tachyarrhythmia as one of a tachyarrhythmia of atrial septal origin and a tachyarrhythmia of ventricular origin using the arrhythmia morphological parameters.

30. The method of claim 29, wherein classifying the tachyarrhythmia as one of the tachyarrhythmia of atrial septal origin and the tachyarrhythmia of ventricular origin using the arrhythmia morphological parameters comprises:
    comparing the arrhythmia morphological parameters to template ventricular tachyarrhythmia morphological parameters; and
    classifying the tachyarrhythmia as the tachyarrhythmia of ventricular origin if the arrhythmia morphological parameters match the template ventricular tachyarrhythmia morphological parameters.

31. The method of claim 30, wherein classifying the tachyarrhythmia as one of the tachyarrhythmia of atrial septal origin and the tachyarrhythmia of ventricular origin using the arrhythmia morphological parameters further comprises classifying the tachyarrhythmia as the tachyarrhythmia of atrial septal origin if the arrhythmia morphological parameters do not match the template ventricular tachyarrhythmia morphological parameters.

32. A method for detecting and classifying tachyarrhythmia in a heart having a right atrium (RA), a left atrium (LA), a left ventricle (LV), a sinoatrial (SA) node, and an atrial septum, the method comprising:
    sensing a plurality of atrial electrograms indicative of regional depolarizations in a plurality of substantially different atrial locations and at least one ventricular electrogram;
    detecting an atrial rate from at least one atrial electrogram of the plurality of atrial electrograms and a ventricular rate from the at least one ventricular electrogram;
    detecting a tachyarrhythmia using at least one of the atrial rate and the ventricular rate;
    classifying the detected tachyarrhythmia as a 1:1 tachyarrhythmia when the atrial rate and the ventricular rate are substantially equal;
    mapping an atrial activation sequence using the plurality of atrial electrograms, the atrial activation sequence indicative of an order of occurrence of regional depolarizations in the plurality of substantially different atrial locations during an atrial depolarization; and
    classifying the 1:1 tachyarrhythmia using the atrial activation sequence.

33. The method of claim 32, wherein sensing the plurality of atrial electrograms comprises:
    sensing an RA electrogram from a location near the SA node;
    sensing an LA electrogram from a location near the LA; and
    sensing an atrial septal electrogram from a location in or near the atrial septum.

34. The method of claim 33, wherein classifying the 1:1 tachyarrhythmia comprises comparing the atrial activation sequence to a plurality of predetermined template sequences.

35. The method of claim 34, wherein classifying the 1:1 tachyarrhythmia comprises classifying the 1:1 tachyarrhythmia as a supraventricular tachyarrhythmia of RA origin if the atrial activation sequence approximately matches a predetermined RA pattern template sequence.

36. The method of claim 34, wherein classifying the 1:1 tachyarrhythmia comprises classifying the 1:1 tachyarrhythmia as a supraventricular tachyarrhythmia of LA origin if the atrial activation sequence approximately matches a predetermined LA pattern template sequence.

37. The method of claim 34, wherein classifying the 1:1 tachyarrhythmia comprises classifying the 1:1 tachyarrhythmia as a supraventricular tachyarrhythmia of atrial septal origin or a ventricular tachyarrhythmia if the atrial activation sequence approximately matches a predetermined atrial septal pattern template sequence.

38. The method of claim 37, wherein classifying the 1:1 tachyarrhythmia further comprises classifying the 1:1 tachyarrhythmia using arrhythmia morphological features extracted from one or more signals selected from the plurality of atrial electrogram and the at least one ventricular electrogram sensed during the detected 1:1 tachyarrhythmia.

39. The method of claim 38, wherein classifying the 1:1 tachyarrhythmia further comprises discriminating the ventricular tachyarrhythmia from the supraventricular tachyarrhythmia of atrial septal origin by comparing the arrhythmia morphological features to predetermined ventricular tachyarrhythmia template morphological features.

40. The method of claim 34, wherein classifying the 1:1 tachyarrhythmia comprises classifying the 1:1 tachyarrhythmia as a supraventricular tachyarrhythmia of atrial septal origin or a ventricular tachyarrhythmia if the atrial activation sequence approximately matches neither the predetermined RA pattern template sequence nor the predetermined LA pattern template sequence.

41. A method for monitoring a heart having a right atrium (RA) connected to a superior vena cava, a left atrium (LA), a sinoatrial (SA) node, an atrial septum, a coronary sinus, and a coronary vein, the method comprising:
- sensing an RA electrogram using an electrode placed in the RA or the superior vena cava near the SA node, the RA electrogram indicative of cardiac depolarizations in an upper RA region including the SA node;
- sensing an LA electrogram using an electrode placed in the coronary sinus or coronary vein near the LA, the LA electrogram indicative of cardiac depolarizations in the LA;
- detecting an RA event from the RA electrogram and an LA event from the LA electrogram for each atrial depolarization;
- measuring an inter-atrial interval between the RA event and the LA event;
- detecting one or more of atrial enlargement and atrial conduction disturbance using the measured inter-atrial interval.

42. The method of claim 41, further comprising prognosticating at least one of atrial fibrillation and heart failure using at least the measured inter-atrial interval.

43. The method of claim 41, farther comprising:
- delivering a therapy; and
- monitoring an effect of the therapy using the inter-atrial interval.

44. The method of claim 41, comprising detecting an abnormal enlargement of at least one of the RA and the LA using the inter-atrial interval.

45. The method of claim 44, wherein detecting the abnormal enlargement of at least one of the RA and the LA comprises:
- comparing the inter-atrial interval to a predetermined threshold interval; and
- indicating the abnormal enlargement of at least one atrium when the inter-atrial interval exceeds the predetermined threshold interval.

46. The method of claim 41, comprising detecting the atrial conduction disturbance using the inter-atrial interval and a threshold.

47. The method of claim 46, wherein detecting the atrial conduction disturbance comprises:
- measuring a variance of the inter-atrial interval;
- comparing the variance of the inter-atrial interval to a predetermined threshold variance; and
- indicating an atrial conduction disturbance when the variance of the inter-atrial interval exceeds the predetermined threshold variance.

* * * * *

UNITED STATES PATENT AND TRADEMARK OFFICE
CERTIFICATE OF CORRECTION

PATENT NO. : 7,328,063 B2
APPLICATION NO. : 11/000133
DATED : February 5, 2008
INVENTOR(S) : Zhang et al.

It is certified that error appears in the above-identified patent and that said Letters Patent is hereby corrected as shown below:

On the title page, item (56), under "Other Publications", in column 2, line 2, delete "Arrythmias" and insert -- Arrhythmias --, therefor.

On the title page, item (56), under "Other Publications", in column 2, line 2, delete "Ventricualr" and insert -- Ventricular --, therefor.

In column 16, line 57, in Claim 6, delete "A" and insert -- The --, therefor.

In column 17, line 37, in Claim 13, after "detector" delete "adapted".

In column 19, line 52, in Claim 29, delete "arrhythmia" and insert -- arrhythmic --, therefor.

In column 19, line 57, in Claim 30, delete "arrhythmia" and insert -- arrhythmic --, therefor.

In column 19, line 58, in Claim 30, delete "arrhythmia" and insert -- arrhythmic --, therefor.

In column 19, line 62, in Claim 30, delete "arrhythmia" and insert -- arrhythmic --, therefor.

In column 20, line 1, in Claim 31, delete "arrhythmia" and insert -- arrhythmic --, therefor.

In column 20, line 3, in Claim 31, delete "arrhythmia" and insert -- arrhythmic --, therefor.

In column 20, line 60, in Claim 38, delete "arrhythmia" and insert -- arrhythmic --, therefor.

UNITED STATES PATENT AND TRADEMARK OFFICE
CERTIFICATE OF CORRECTION

PATENT NO. : 7,328,063 B2
APPLICATION NO. : 11/000133
DATED : February 5, 2008
INVENTOR(S) : Zhang et al.

It is certified that error appears in the above-identified patent and that said Letters Patent is hereby corrected as shown below:

In columns 20-21, lines 67-1, in Claim 39, delete "arrhythmia" and insert -- arrhythmic --, therefor.

In column 22, line 1, in Claim 43, delete "farther" and insert -- further --, therefor.

Signed and Sealed this

Twentieth Day of May, 2008

JON W. DUDAS
*Director of the United States Patent and Trademark Office*